United States Patent
Kelton et al.

(10) Patent No.: US 8,512,685 B2
(45) Date of Patent: Aug. 20, 2013

(54) HAIR LIGHTENING COMPOSITION CONTAINING POLYMER FILM

(75) Inventors: Christine Kelton, Covington, KY (US); Vincent Fischer, St. Petersburg, FL (US)

(73) Assignee: Kao USA Inc., Cincinnati, OH (US)

( * ) Notice: Subject to any disclaimer, the term of this patent is extended or adjusted under 35 U.S.C. 154(b) by 36 days.

(21) Appl. No.: 12/938,470

(22) Filed: Nov. 3, 2010

(65) Prior Publication Data

US 2011/0104090 A1 May 5, 2011

Related U.S. Application Data

(60) Provisional application No. 61/257,976, filed on Nov. 4, 2009.

(51) Int. Cl.
- *A61K 8/72* (2006.01)
- *A61Q 5/08* (2006.01)
- *A61Q 5/12* (2006.01)

(52) U.S. Cl.
USPC .............. 424/62; 424/70.11; 8/406; 526/306; 526/307

(58) Field of Classification Search
USPC .................. 424/62, 70; 526/306, 307; 8/406
See application file for complete search history.

(56) References Cited

U.S. PATENT DOCUMENTS

| | | | |
|---|---|---|---|
| 4,733,677 A | 3/1988 | Gee et al. | |
| 5,104,642 A | 4/1992 | Wells et al. | |
| 6,156,077 A * | 12/2000 | Shibata et al. | 8/406 |
| 6,540,791 B1 * | 4/2003 | Dias | 8/111 |
| 2004/0205908 A1* | 10/2004 | Lim et al. | 8/405 |
| 2008/0131392 A1* | 6/2008 | Hoffmann | 424/70.11 |
| 2009/0175804 A1 | 7/2009 | Jennings et al. | |
| 2009/0214447 A1 | 8/2009 | Jennings et al. | |

FOREIGN PATENT DOCUMENTS

| | | |
|---|---|---|
| EP | 1 878 469 | 1/2008 |
| WO | WO 2009/080670 | 7/2009 |
| WO | WO 2009/109345 | 9/2009 |

\* cited by examiner

*Primary Examiner* — Fereydoun G Sajjadi
*Assistant Examiner* — Anna Falkowitz
(74) *Attorney, Agent, or Firm* — Frost Brown Todd LLC

(57) ABSTRACT

Aqueous hair care compositions which provide hair styling, hair lightening and hair conditioning benefits are disclosed. The compositions provide hair lightening effects greater than that which would typically be achieved using hydrogen peroxide solutions alone. The compositions comprise a stabilized oxidative compound, a film-forming hair care polymer, a cationic hair care polymer, and water. The method of conditioning, styling and coloring hair utilizing the disclosed compositions is also disclosed.

20 Claims, No Drawings

HAIR LIGHTENING COMPOSITION CONTAINING POLYMER FILM

This application is related to and claims priority from U.S. Provisional Patent Application 61/257,976, Kelton and Fischer, filed Nov. 4, 2009.

TECHNICAL FIELD

The present invention relates to compositions and methods used for coloring (particularly lightening), conditioning and styling hair.

BACKGROUND

Personal appearance is very important and having hair that looks good and stylish is an important part of personal grooming and personal appearance. To that end, hair styling compositions, hair coloring (particularly hair lightening) compositions and hair conditioning compositions are widely used. Hair lightening (i.e., lightening the color of hair to make it "lighter" or "blonder", either for the entire head of hair or for certain areas of the hair (e.g., streaking) is a technique that is frequently used and highly desired.

It is generally thought to be advantageous to combine various hair care functions into a single product so that fewer products are required for purchase and use. An example of this is the shampoo plus conditioner products (2-in-1 shampoos) which have become quite popular. This provides greater convenience for the consumer (for example, a conditioner that lightens and/or styles hair, or a styling composition that lightens and/or conditions hair). The present invention combines hair styling, lightening and conditioning effects into a single composition and, in fact, provides a hair lightening effect which is greater than that which would typically be achieved using a hydrogen peroxide solution alone.

Thus, the compositions of the present invention contain hydrogen peroxide or a suitable stabilized oxidative compound which is capable of oxidizing hair melanin, in combination with a pair of polymers with one polymer being cationic in nature and the other polymer being a film-former (such as copolymers of polyvinylpyrrolidone) which, when applied to hair, results in: (a) a color lightening effect greater than that which can be achieved using a comparable hydrogen peroxide solution alone, (b) conditioning and detangling benefits, and (c) hairstyling properties. It is believed that the polymer combination leads to a lowering of the solution surface tension easing the wettability and dispersion on the hair while aiding in detangling and providing conditioning benefits. It is further believed that the film-former (fixative) polymer forms a semi-occlusive film leading to enhanced diffusion of the oxidizer into the hair, as well as providing hairstyling benefits. When combined with the use of high heat (for example, from a flat iron, curling iron or blow dryer) or exposure to UV light (natural or artificial), an even greater effect, both in terms of lightening of the melanin and hair conditioning properties, can be achieved.

PCT Published Patent Application WO 2009/080670, Lagrand et al, published Jul. 2, 2009, defines hair bleaching compositions which contain an alkanolamine, an amino acid, and polyethoxylated sorbitan esters. Compositions containing cationic conditioner polymers (polyquats) are disclosed. However, there does not appear to be any suggestion to include styling polymers in the defined compositions.

PCT Published Patent Application WO 2009/109345, Pratt et al, published Sep. 11, 2009, defines hair bleaching compositions which are said to minimize development of heat during the bleaching operation. The compositions include at least one compound with a bleaching and/or highlighting effect, and a calcium salt. The exemplified compositions include a bleaching compound together with a cationic polymer, but do not include a hairstyling polymer.

EPO Published Patent Application EP 1 878 469, Bureiko et al, published Jan. 16, 2008, defines hair coloring and bleaching compositions which are said to provide improved lift, lightening and color delivery, while minimizing damage and scalp sensory irritation. The compositions comprise a peroxide and a thickening gel network which includes a mixture of high and low HLB nonionic surfactants. The application includes a general disclosure of polymers including cationic polymers, but includes no disclosure or exemplification of hair styling polymers or of combinations of cationic polymers and styling polymers.

U.S. Published Patent Application 2009/0175804, Jennings et al, published Jul. 9, 2009, defines a class of new cationic hair care polymers which may be used in hair care compositions to provide styling and conditioning benefits. The application includes generic language regarding hair coloring compositions. Example 63 discloses the use of the new cationic polymers together with a cationic hair care polymer material (polyquat-6) in a hair conditioner composition. The application does not appear to suggest the inclusion of styling polymers in those compositions.

U.S. Published Patent Application 2009/0214447, Jennings et al, published Aug. 27, 2009, describes cationic nanoparticles which may be used in hair care products for providing conditioning benefits. The application includes an incidental mention of hair dying compositions. The application does not appear to include a disclosure of hair styling polymers or of a combination of cationic polymers and hair styling polymers in a peroxide-containing composition.

Although hair lightening compositions, such as Nordic Blonde and Sun-In are commercially available, those compositions, while including hydrogen peroxide, do not appear to include a combination of cationic polymers and hair styling polymers as is required by the present invention.

SUMMARY

The present invention relates to aqueous hair treatment compositions, having a pH of from about 2 to about 4, comprising:
(a) from about 0.1% to about 10% of a stabilized oxidative compound capable of oxidizing hair melanin;
(b) from about 0.01% to about 1.0% of a film-forming hair care polymer which is solubilized or dispersed in the composition so as to provide a uniform dispersion of the polymer on the hair;
(c) from about 0.01% to about 1.0% of a cationic hair care polymer which is solubilized or dispersed in the composition so as to provide a uniform dispersion of the cationic polymer on the hair; and
(d) water.

An example of the oxidative compound is hydrogen peroxide; an example of the film-forming polymer is a copolymer of vinyl acetate and polyvinylpyrrolidone; and an example of the cationic polymer is a terpolymer of acrylic acid, methacrylamidopropyl trimethyl ammonium chloride and methyl acrylate (polyquaternium-47).

The method of conditioning and coloring hair by applying to said hair and effective amount of the composition defined above is also claimed.

All ratios and percentages given herein are "by weight" unless otherwise specified. In addition, all ratios and percentages herein are on an "active content" basis. Further, all references which are described in this application are incorporated by reference herein.

DETAILED DESCRIPTION

The present invention relates to aqueous hair treatment compositions which comprise (a) a stabilized compound capable of oxidizing hair melanin; (b) a film-forming hair care polymer; (c) a cationic hair care polymer; and (d) water. The composition is an aqueous composition which means that the vehicle is either water or is primarily water together with other solvents. Generally, the compositions of the present invention comprise from about 40% to about 95% (for example, from about 70% to about 95%) water. The compositions generally have a pH of from about 2 to about 4 (for example, from about 2.7 to about 3.3); this pH primarily acts to stabilize the oxidative compound in the composition. The pH can be achieved by incorporating a buffering system in the composition to maintain the desired pH. Phosphoric acid and/or disodium phosphate are useful buffers, particularly when the oxidative material is hydrogen peroxide. A buffering system comprising some or all of etidronic acid, sodium hydroxide, salicylic acid, and acetaminophen may also be used.

The compositions of the present invention include a suitable oxidative compound capable of oxidizing hair melanin. Since the compositions of the present invention are going to be used on human hair, the oxidizing compounds (as well as the entire composition) must be safe for application to human hair, skin and scalp. The compositions include from about 0.1% to about 10% (for example, from about 3.5% to about 4.5%) by weight of the oxidizing compound. Examples of such oxidizing compounds include hydrogen peroxide, persulfate salts (e.g., ammonium, potassium and sodium), and bromate salts (e.g., sodium and potassium), as well as mixtures of those materials. Hydrogen peroxide ($H_2O_2$) is a material frequently used in the compositions of the present invention. Compositions containing oxidative compounds need to be properly stabilized to prevent degradation.

Film-forming hair care polymers (i.e., hair styling polymers) are also included in the compositions of the present invention. The film-forming polymers should be water-soluble, water-dispersible, and/or able to be solubilized in the composition vehicle to allow for uniform dispersion of the polymer when the composition is applied to the hair. The polymers generally can be nonionic or pseudocationic in nature and are well-known for use in hair care compositions. They should be safe for application to the hair, skin and scalp. Examples of such polymers are found in U.S. Pat. No. 5,104,642, Wells et al, issued Apr. 14, 1992, and Cosmetic Science Technology, 2005, 142, both of which are incorporated herein by reference. Non-limiting examples of such film-forming polymers (as well as mixtures of those polymers) are defined below:

Polyvinylpyrrolidone (PVP)—examples of such materials include International Specialty Products (ISP) products such as PVP K-15, PVP K-30, PVP K-60, PVP K-90, and PVP K-120.

Copolymers of vinylpyrrolidone (VP) including vinyl acetates and crotonic acid (for example, ISP products, such as PVP/VA W-635 and PVP/VA W-735).

Isobutylene/dimethylaminopropyl maleimide/ethoxylated maleimide/maleic acid copolymers (examples include ISP products, such as Aquaflex XL-30).

Terpolymers of vinylacetate, mono-n-butyl maleate and isobornyl acrylate (examples include ISP products, such as Advantage Plus).

VP/dimethylaminoethylmethacrylate copolymers (examples include ISP products, such as copolymer 937 and copolymer 958).

Modified corn starch (examples include Akzo Nobel products, such as Amaze).

Mixtures of these polymers can be used. An example of a film-forming polymer which can be used in the compositions of the present invention are copolymers of vinylacetate and polyvinylpyrrolidone (PVP). The film-forming polymers are included in the compositions of the present invention at from about 0.01% to about 1% by weight of the composition (for example, from about 0.4% to about 0.6%).

The compositions of the present invention also include cationic hair care polymers which are frequently used in hair styling and conditioning compositions. The cationic polymers are included at from about 0.01% to about 1.0% by weight of the composition (for example, from about 0.4% to about 0.6%). The cationic polymers should be water-soluble, dispersible and/or able to be solubilized in the composition vehicle to allow for a uniform dispersion of the cationic polymer when the composition is applied to the hair. Mixtures of these polymers can also be utilized. The polymers should be safe for application to the hair, skin and scalp. Non-limiting examples of cationic polymers are disclosed in Int. J. Cosmetic Sci. 5:181-188 (1983); and U.S. Pat. No. 4,733,677, Gee et al, issued Mar. 29, 1988; both incorporated herein by reference. Examples of cationic polymers which can be used in the compositions of the present invention include the following:

Copolymers of acrylamide and quaternized dimethylammoniumethyl methacrylate (polyquaternium-5)

Poly-diallydimethylammonium chloride (polyquaternium-6)

Copolymer of acrylamide and dimethylammonium chloride (polyquaternium-7)

Quaternized hydroxyethylcellulose (polyquaternium-10)

Copolymer of vinylpyrrolidone and quaternized dimethylaminoethyl methyacrylate (polyquaternium-11)

Acrylamide-dimethylaminoethyl methyacrylate methyl chloride copolymer (polyquaternium-15)

Copolymer of vinylpyrrolidone and quaternized vinyl imidazole (polyquaternium-16)

Copolymer of acrylic acid and dialkyldimethylammonium chloride (polyquaternium-22)

Copolymer of vinylpyrrolidone and methacrylamidopropyl trimethylammonium (polyquaternium-28)

Terpolymer of acrylic acid, acrylamide and diallyldimethylammonium chloride (polyquaternium-39)

Terpolymer of vinylcaprolactam, vinylpyrrolidone and quaternized vinylimidazole (polyquaternium-46)

Terpolymer of acrylic acid, methacrylamidopropyl trimethyl ammonium chloride and methyl acrylate (polyquaternium-47)

Terpolymer of vinylpyrrolidone, dimethylaminopropyl methacrylamide and methacryloylaminopropyl lauryldimonium chloride (polyquaternium-55)

An example of a cationic polymer material which can be used in the compositions of the present invention are the terpolymers of acrylic acid, methacrylamidopropyl trimethyl ammonium chloride and methyl acrylate (polyquaternium-47).

Other conventionally used components found in hair care compositions can be incorporated into the compositions of the present invention at their art-established levels. For example, surfactants (such as nonionic surfactants, including polyethyloxylated alcohols such as Tweens) can be utilized in order to get and keep the composition components in solution. Additional conditioning agents (such as quaternium ammonium materials or silicones), vitamins and botanical extracts can also be included in the compositions. In addition, aesthetic and formulational materials, such as fragrances, pH adjusters, buffers, solubilizers (e.g., polysorbate 20), colorants and preservatives can be included in the compositions.

The present application also encompasses a method for conditioning and coloring hair by applying to said hair an effective amount of the compositions described herein. As used herein, the phrase "effective amount" denotes an amount of the oxidative compound, film-forming polymer and cationic polymer which is sufficient to provide the hair conditioning, styling and hair lightening benefits defined herein, without resulting in any significant side-effects to the user, such as scalp or skin irritation. The compositions of the present invention can be applied using any known techniques for application of such compositions to the hair. For example, the compositions can be applied using a spray, such as a pump spray or an aerosol spray; using an applicator (such as a brush or a foam pad), can be combed into the hair, or can be worked into the hair with the fingers as a liquid as one would do with a leave-in conditioner or styling product. Clearly, the more pinpointed application, such as application with a brush or foam applicator, would be desirable when streaking or highlighting is desired rather than lightening of the full head of hair.

Although not intending to be bound by theory, it is believed that the film-forming/cationic polymer combination utilized in the compositions of the present invention leads to a lowering of the solution surface tension of the composition, easing the wettability and dispersion on the hair of the oxidizing material, while aiding and detangling and providing conditioning benefits. It is further believed that the film-former (fixative) polymer forms a semi-occlusive film which provides enhanced diffusion of the oxidizer into the hair, as well as providing hair styling benefits. The compositions of the present invention may be combined with the use of high heat (such as that provided by a flat iron, curling iron or blow dryer) or exposure to UV light (either natural or artificial) in order to achieve an even greater effect (both in terms of hair lightening of the melanin and hair conditioning properties).

The compositions of the present invention can be made utilizing processes well-known in the art. A generalized process for making the compositions of the present invention is as follows:

Add deionized water to the main tank. Disperse buffering agents into the water and stir until fully dissolved. Then add in polymers one by one, allowing for homogeneity before adding the next ingredient. A premix of a solubilizer and the fragrance is made, and then added to the main tank. The oxidizer can be added last. It is important that the solution has been properly acidified and is at room temperature or below before the addition of the oxidizing agent. At this point, other aesthetic ingredients, such as color, extracts, etc., may be added to the formula if desired. Care must be taken to ensure that all surfaces that will come in contact with the oxidizer are properly passivated.

EXAMPLE 1

A composition of the present invention includes the following components:

| INCI Name | Trade Name | W/W % |
| --- | --- | --- |
| Deionized water | N/A | 89.8495 |
| Hydrogen Peroxide (50% active) | N/A | 8.00 |
| Polyquaternium-47 (21% active) | Nalco Merquat 2001 | 0.50 |
| VP/VA Copolymer (50% active) | ISP W735 | 0.50 |
| Fragrance solubilizer | N/A | 0.40 |
| Disodium Phosphate | N/A | 0.30 |
| Phosphoric Acid | N/A | 0.30 |
| Fragrance | N/A | 0.13 |
| Polyquaternium-55 | N/A | 0.01 |
| Water (and) Propylene Glycol (and) Botanical Extracts (and) Glycerin (and) Alcohol (and) PEG-40 Hydrogenated Castor Oil (and) Tocopherol | N/A | 0.01 |
| Colorant | N/A | 0.0005 |
|  |  | 100.0000 |

The composition is made as follows:

Care must be taken to ensure that all surfaces that will come in contact with the formula are properly passivated. Add deionized water to the main tank large enough to hold the whole batch. Disperse the buffering agents into the water and stir until fully dissolved. Add the cationic polymer and mix until homogeneous. Add the fixative polymer and mix until homogeneous. Add remaining polymer and botanical extracts and mix thoroughly. In a suitably-sized container, a premix of a solubilizer and the fragrance is made, and then is added to the main tank. Carefully add the hydrogen peroxide to the main tank while making sure to avoid splashing. Mix until completely homogeneous. Then, in a suitably-sized premix vessel, add deionized water and colorant and mix until dissolved, then add this mixture to the main tank. It is important that the solution has been properly acidified and is at room temperature or below before the addition of the hydrogen peroxide.

When applied to hair, for example using a pump spray, the composition provides hair lightening, hair styling and hair conditioning benefits to the user. The benefits can be enhanced by blow drying the hair with heat, and/or using additional heat appliances, such as a flat iron, curling iron or hot rollers, after the product has been applied.

EXAMPLE 2

A composition of the present invention includes these components and is made as follows:

| INCI Name | Trade Name | W/W % |
| --- | --- | --- |
| Deionized water | N/A | 90.1745 |
| Hydrogen Peroxide (50% active) | N/A | 8.00 |
| Polyquaternium-47 (21% active) | Nalco Merquat 2001 | 0.50 |
| VP/VA Copolymer (50% active) | ISP W735 | 0.50 |
| Fragrance solubilizer | N/A | 0.40 |
| Etidronic Acid | N/A | 0.1330 |
| Fragrance | N/A | 0.13 |
| Sodium Hydroxide | N/A | 0.0960 |
| Phosphoric Acid | N/A | 0.0160 |
| Salicylic Acid | N/A | 0.0150 |
| Acetaminophen | N/A | 0.0150 |
| Polyquaternium-55 | N/A | 0.01 |

-continued

| INCI Name | Trade Name | W/W % |
| --- | --- | --- |
| Water (and) Propylene Glycol (and) Botanical Extracts (and) Glycerin (and) Alcohol (and) PEG-40 Hydrogenated Castor Oil (and) Tocopherol | N/A | 0.01 |
| Colorant | N/A | 0.0005 |
| | | 100.0000 |

Care must be taken to ensure that all surfaces that will come in contact with the formula are properly passivated. Add deionized water to tank large enough to hold the whole batch. Add the etidronic acid and mix until homogeneous. In a suitably sized pre-mix vessel, add deionized water, sodium hydroxide, salicylic acid and acetaminophen, and thoroughly mix until all ingredients are dissolved and homogeneous. Add to the main tank with mixing. Add the following ingredients to the main tank, one at a time, allowing each to thoroughly mix until homogeneous before adding the next ingredient: polyquaternium-47 and VP/VA copolymer. Add remaining polymer and botanical extracts and mix thoroughly. In a suitably-sized pre-mix vessel, add the fragrance solubilizer and fragrance and thoroughly mix for 10 minutes until completely homogeneous, then add to main tank. Carefully add the hydrogen peroxide to the main tank while making sure to avoid splashing. Mix until completely homogeneous, or for about 10 minutes. In a suitably-sized pre-mix vessel, add deionized water and colorant and mix until completely dissolved, then add to the main tank and let mix for 10 minutes. Add the phosphoric acid to the main tank and allow to mix for 5 minutes. It is important that the solution has been properly acidified and is at room temperature or below before the addition of the hydrogen peroxide.

When applied to hair, the composition provides hair lightening, hair styling and hair conditioning benefits to the user.

EXAMPLE 3

A composition of the present invention includes the following components:

| INCI Name | Trade Name | W/W % |
| --- | --- | --- |
| Deionized water | N/A | 89.8195 |
| Hydrogen Peroxide (50% active) | N/A | 8.00 |
| Polyquaternium-11 (20% active) | ISP Gafquat 755N | 0.53 |
| VP/VA Copolymer (50% active) | ISP W735 | 0.50 |
| Fragrance solubilizer | N/A | 0.40 |
| Disodium Phosphate | N/A | 0.30 |
| Phosphoric Acid | N/A | 0.30 |
| Fragrance | N/A | 0.13 |
| Polyquaternium-55 | N/A | 0.01 |
| Water (and) Propylene Glycol (and) Botanical Extracts (and) Glycerin (and) Alcohol (and) PEG-40 Hydrogenated Castor Oil (and) Tocopherol | N/A | 0.01 |
| Colorant | N/A | 0.0005 |
| | | 100.0000 |

EXAMPLE 4

A composition of the present invention includes the following components:

| INCI Name | Trade Name | W/W % |
| --- | --- | --- |
| Deionized water | N/A | 90.0995 |
| Hydrogen Peroxide (50% active) | N/A | 8.00 |
| Polyquaternium-47 (21% active) | Nalco Merquat 2001 | 0.50 |
| Fragrance Solubilizer | N/A | 0.40 |
| Disodium Phosphate | N/A | 0.30 |
| Phosphoric Acid | N/A | 0.30 |
| PVP (100% active) | ISP PVP K90 | 0.25 |
| Fragrance | N/A | 0.13 |
| Polyquaternium-55 | N/A | 0.01 |
| Water (and) Propylene Glycol (and) Botanical Extracts (and) Glycerin (and) Alcohol (and) PEG-40 Hydrogenated Castor Oil (and) Tocopherol | N/A | 0.01 |
| Colorant | N/A | 0.0005 |
| | | 100.0000 |

EXAMPLE 5

A composition of the present invention includes the following components:

| INCI Name | Trade Name | W/W % |
| --- | --- | --- |
| Deionized water | N/A | 87.4695 |
| Hydrogen Peroxide (50% active) | N/A | 8.00 |
| Polyquaternium-47 (21% active) | Nalco Merquat 2001 | 2.38 |
| VP/VA Copolymer (50% active) | ISP W735 | 1.00 |
| Fragrance solubilizer | N/A | 0.40 |
| Disodium Phosphate | N/A | 0.30 |
| Phosphoric Acid | N/A | 0.30 |
| Fragrance | N/A | 0.13 |
| Polyquaternium-55 | N/A | 0.01 |
| Water (and) Propylene Glycol (and) Botanical Extracts (and) Glycerin (and) Alcohol (and) PEG-40 Hydrogenated Castor Oil (and) Tocopherol | N/A | 0.01 |
| Colorant | N/A | 0.0005 |
| | | 100.0000 |

The compositions described in Examples 3, 4 and 5 are made as follows:

Care must be taken to ensure that all surfaces that will come in contact with the formula are properly passivated. Add deionized water to the main tank large enough to hold the whole batch. Disperse the buffering agents into the water and stir until fully dissolved. Add the cationic polymer and mix until homogeneous. Add the fixative polymer and mix until homogeneous. Add remaining polymer and botanical extracts and mix thoroughly. In a suitably-sized container, a pre-mix of fragrance solubilizer and the fragrance is made, and then is added to the main tank. Carefully add the hydrogen peroxide to the main tank while making sure to avoid splashing. Mix until completely homogeneous. Then, in a suitably-sized pre-mix vessel, add deionized water and colorant and mix until dissolved, then add this mixture to the main tank. It is important that the solution has been properly acidified and is at room temperature or below before the addition of the hydrogen peroxide.

When applied to hair, the compositions described in Examples 3, 4 and 5 provide hair lightening, hair styling and hair conditioning benefits to the user.

What is claimed is:

1. An aqueous hair treatment composition in the form of a single composition which is applied directly to hair without premixing, having a pH of from about 2 to about 4, comprising the following components which are mixed prior to packaging:
   (a) from about 0.01% to about 10% of a stabilized oxidative compound capable of oxidizing hair melanin;
   (b) from about 0.01% to about 1.0% of a film-forming hair care polymer which is solubilized or dispersed in the composition so as to provide a uniform distribution of the film-forming polymer on the hair;
   (c) from about 0.01% to about 1.0% of a cationic hair care polymer which is solubilized or dispersed in the composition so as to provide a uniform dispersion of the cationic polymer on the hair; and
   (d) water.

2. A composition according to claim 1 wherein the oxidative compound is selected from the group consisting of peroxides, persulfate salts, bromate salts, and mixtures thereof.

3. A composition according to claim 2 wherein the film-forming polymer is selected from the group consisting of nonionic polymers, pseudocationic polymers, and mixtures thereof.

4. The composition according to claim 3 wherein the film-forming polymer is selected from the group consisting of polyvinylpyrrolidone; copolymers of vinylpyrrolidone;
   isobutylene/dimethylaminopropyl maleimide/ethoxylated maleimide/maleic acid copolymers;
   terpolymers of vinyl acetate, mono-n-butyl maleate and isobornyl acrylate;
   vinylpyrrolidone/dimethylaminoethyl methacrylate copolymers; modified corn starch; and mixtures thereof.

5. The compositions according to claim 3 wherein the film-forming polymer is a cationic polymer is selected from the group consisting of:
   copolymers of acrylamide and quatemized dimethylammoniumethyl methacrylate;
   poly-diallydimethylammonium chloride;
   copolymers of acrylamide and diallyldimethylammonium chloride;
   quaternized hydroxyethylcellulose;
   copolymers of vinylpyrrolidone and quaternized dimethylaminoethyl methacrylate;
   acrylamide-dimethylaminoethyl methacrylate methyl chloride copolymers;
   copolymers of vinylpyrrolidone and quaternized vinylimidazole;
   copolymers of acrylic acid and diallyldimethylammonium chloride;
   copolymers of vinylpyrrolidone and methacrylamidopropyl trimethylammonium;
   terpolymers of acrylic acid, acrylamide and diallyldimethylammonium chloride;
   terpolymers of vinylcaprolactam, vinylpyrrolidone and quatemized vinylimidazole;
   terpolymers of acrylic acid, methacrylamidopropyl trimethyl ammonium chloride and methyl acrylate;
   terpolymers of vinylpyrrolidone, dimethylaminopropyl methacrylamide, and methacryloyl -aminopropyl lauryldimonium chloride;
   and mixtures thereof.

6. The composition according to claim 3 which additionally comprises a buffering system for the oxidative compound.

7. The compositions according to claim 6 wherein the oxidative compound is selected from the group consisting of hydrogen peroxide, ammonium persulfate, potassium persulfate, sodium persulfate, sodium bromate, potassium bromate, and mixtures thereof.

8. The compositions according to claim 7 wherein the oxidative compound is hydrogen peroxide.

9. The compositions according to claim 8 wherein the buffer is selected from the group consisting of phosphoric acid, disodium phosphate, and mixtures thereof.

10. The compositions according to claim 8 wherein the buffer is selected from the group consisting of etidronic acid, sodium hydroxide, salicylic acid, acetaminophen and mixtures thereof.

11. The compositions according to claim 8 wherein the film-forming polymer is a copolymer of vinylacetate and polyvinylpyrrolidone.

12. The compositions according to claim 8 wherein the film-forming polymer comprises a terpolymer of acrylic acid, methacrylamidopropyl trimethylammonium chloride and methylacrylate (polyquaternium-47).

13. The compositions according to claim 8 wherein the pH of the composition is from about 2.7 to about 3.3.

14. The compositions according to claim 8 which comprises from about 3.5% to about 4.5% by weight of hydrogen peroxide.

15. The compositions of claim 14 which comprises from about 0.4% to about 0.6% by weight of the film-forming polymer.

16. The compositions according to claim 15 which comprises from about 0.4% to about 0.6% by weight of the cationic polymer.

17. A method of treating hair by applying to said hair an effective amount of the composition according to claim 1.

18. A method of treating hair by applying to said hair an effective amount of the composition according to claim 12.

19. The method according to claim 17 comprising the following additional step:
   exposing the hair carrying the composition to heat or UV light.

20. The method according to claim 19 wherein the heat is applied to the hair by flat iron, curling iron, blow dryer, or combinations thereof.

* * * * *